(12) United States Patent
Meyer et al.

(10) Patent No.: US 8,318,946 B2
(45) Date of Patent: Nov. 27, 2012

(54) PROCESS FOR THE PREPARATION OF 2-SUBSTITUTED-5-(1-ALKYLTHIO) ALKYLPYRIDINES

(75) Inventors: Kevin G. Meyer, Zionsville, IN (US); Kim E. Arndt, Carmel, IN (US)

(73) Assignee: Dow Agrosciences, LLC, Indianapolis, IN (US)

( * ) Notice: Subject to any disclaimer, the term of this patent is extended or adjusted under 35 U.S.C. 154(b) by 355 days.

(21) Appl. No.: 12/722,925

(22) Filed: Mar. 12, 2010

(65) Prior Publication Data

US 2010/0168435 A1 Jul. 1, 2010

Related U.S. Application Data

(62) Division of application No. 11/704,796, filed on Feb. 9, 2007, now Pat. No. 7,709,648.

(51) Int. Cl.
  *C07D 211/90* (2006.01)
(52) U.S. Cl. ...................................................... 546/318
(58) Field of Classification Search .................... 546/318
  See application file for complete search history.

(56) References Cited

U.S. PATENT DOCUMENTS

| | | |
|---|---|---|
| 3,711,486 A | 1/1973 | Torba et al. |
| 3,787,420 A | 1/1974 | Torba et al. |
| 3,852,279 A | 12/1974 | Krapcho et al. |
| 4,692,184 A | 9/1987 | Lee |
| 4,747,871 A | 5/1988 | Ruminski et al. |
| 4,948,896 A | 8/1990 | Nagao |
| 4,973,695 A | 11/1990 | Yamashita et al. |
| 5,053,516 A | 10/1991 | Hartmann et al. |
| 5,099,023 A | 3/1992 | Miller et al. |
| 5,099,024 A | 3/1992 | Pulwer et al. |
| 5,118,809 A | 6/1992 | Cevasco et al. |
| 5,124,458 A | 6/1992 | Cevasco et al. |
| 5,169,432 A | 12/1992 | Auinbauh et al. |
| 5,225,560 A | 7/1993 | Cevasco et al. |
| 5,227,491 A | 7/1993 | Doehner, Jr. |
| 5,229,519 A | 7/1993 | Zhang et al. |
| 6,673,938 B1 * | 1/2004 | Edmunds et al. ............. 546/318 |
| 7,511,149 B2 | 3/2009 | Arndt et al. |
| 7,541,469 B2 | 6/2009 | Renga et al. |
| 7,604,815 B2 | 10/2009 | Loso et al. |
| 7,678,920 B2 | 3/2010 | Zhu et al. |
| 2003/0078430 A1 | 4/2003 | Satake et al. |
| 2004/158067 A1 | 8/2004 | Hutchison et al. |
| 2006/0199964 A1 | 9/2006 | Jackson et al. |
| 2007/0203191 A1 | 8/2007 | Loso et al. |
| 2007/0249837 A1 | 10/2007 | Gebhardt et al. |
| 2007/0299264 A1 | 12/2007 | Huang et al. |
| 2008/0108665 A1 | 5/2008 | Huang et al. |
| 2008/0108666 A1 | 5/2008 | Loso et al. |
| 2008/0108667 A1 | 5/2008 | Zhu et al. |
| 2008/0132705 A1 | 6/2008 | Heller et al. |
| 2008/0280915 A1 | 11/2008 | Loso et al. |

FOREIGN PATENT DOCUMENTS

| | | |
|---|---|---|
| WO | WO/2007003779 | 1/2007 |
| WO | WO/2007/095229 | 8/2007 |
| WO | WO/2008/057131 | 5/2008 |
| WO | WO/2008057131 | 5/2008 |
| WO | WO2007003779 | 1/2009 |

OTHER PUBLICATIONS

Singer, Alvin; McElvain, S.M. 2,6-Dimethylpyridine. Organic Syntheses, 1934, 14, 30.

* cited by examiner

*Primary Examiner* — David K O'Dell
(74) *Attorney, Agent, or Firm* — Carl D. Corvin

(57) ABSTRACT

2-Substituted-5-(1-alkylthio)alkylpyridines are produced efficiently and in high yield.

2 Claims, No Drawings

PROCESS FOR THE PREPARATION OF 2-SUBSTITUTED-5-(1-ALKYLTHIO) ALKYLPYRIDINES

This application is a divisional of U.S. non-provisional application Ser. No. 11/704,796 filed on 9 Feb. 2007. The disclosure of application Ser. No. 11/704,796 is hereby incorporated, in its entirety, by reference.

BACKGROUND OF THE INVENTION

The present invention concerns processes for preparation of 2-substituted-5-(1-alkylthio)alkylpyridines.

The 2-substituted-5-(1-alkylthio)alkylpyridines are useful intermediates for the preparation of certain new insecticides; see, for example, U.S. Patent Publication 2005/0228027. It would be advantageous to produce 2-substituted-5-(1-alkylthio)alkylpyridines efficiently and in high yield.

SUMMARY OF THE INVENTION

One aspect of the present invention concerns a process for the preparation of 2-substituted-5-(1-alkylthio)alkylpyridine (I),

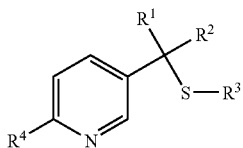

wherein $R^1$ and $R^2$ independently represent H, $C_1$-$C_4$ alkyl, or either of $R^1$ or $R^2$ taken together with $R^3$ represent a 4- to 6-membered saturated ring, or $R^1$ taken together with $R^2$ represent a 3- to 6-membered saturated ring optionally substituted with an O or a N atom;

$R^3$ represents $C_1$-$C_4$ alkyl or $R^3$ taken together with either of $R^1$ or $R^2$ represent a 4- to 6-membered saturated ring; and $R^4$ represents $C_1$-$C_4$ alkyl or $C_1$-$C_4$ haloalkyl;

which comprises:

a) condensing a substituted enone (II),

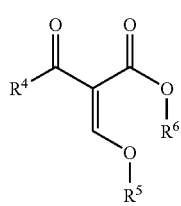

wherein $R^4$ is as previously defined; and
$R^5$ and $R^6$ independently represent $C_1$-$C_4$ alkyl;
with an enamine (III),

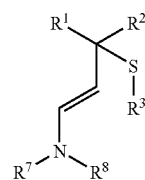

wherein $R^1$, $R^2$ and $R^3$ are as previously defined; and
$R^7$ and $R^8$ independently represent $C_1$-$C_4$ alkyl or $R^7$ and $R^8$ taken together with N represent a 5-membered saturated or unsaturated ring;

b) cyclizing the reaction mixture from step a) in the presence of ammonia or a reagent capable of generating ammonia to produce a 2,3,5-substituted pyridine (IV),

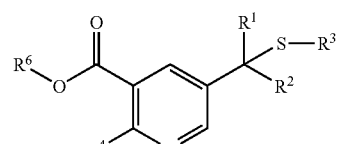

wherein $R^1$, $R^2$, $R^3$, $R^4$ and $R^6$ are as previously defined; and c) saponifying and decarboxylating the 2,3,5-substituted pyridine (IV) to give 2-substituted-5-(1-alkylthio)alkylpyridine (I). This method is particularly well suited to prepare compounds in which $R^4$ represents $CF_3$.

Another aspect of the invention concerns the intermediate nicotinic acid derivatives of the Formula (IV)

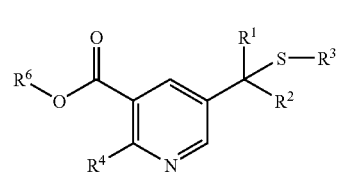

wherein $R^1$ and $R^2$ independently represent H, $C_1$-$C_4$ alkyl, or either of $R^1$ or $R^2$ taken together with $R^3$ represent a 4- to 6-membered saturated ring, or $R^1$ taken together with $R^2$ represent a 3- to 6-membered saturated ring optionally substituted with an O or a N atom;

$R^3$ represents $C_1$-$C_4$ alkyl or $R^3$ taken together with either of $R^1$ or $R^2$ represent a 4- to 6-membered saturated ring;

$R^4$ represents $C_1$-$C_4$ alkyl or $C_1$-$C_4$ haloalkyl; and
$R^6$ represents H or $C_1$-$C_4$ alkyl.

DETAILED DESCRIPTION OF THE INVENTION

Unless specifically limited otherwise, the term "alkyl" (including derivative terms such as "haloalkyl"), as used herein, include straight chain, branched chain, and cyclic groups.

Thus, typical alkyl groups are methyl, ethyl, 1-methylethyl, propyl, 1,1-dimethylethyl, and cyclopropyl. The term "halogen" includes fluorine, chlorine, bromine and iodine. The term "haloalkyl" includes alkyl groups substituted with any number from one to the maximum possible number of halogen atoms.

One aspect of the present invention concerns a process for the preparation of 2-substituted-5-(1-alkylthio)alkylpyridine (I),

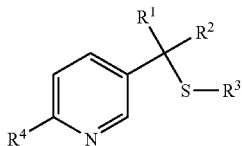

(I)

wherein $R^1$ and $R^2$ independently represent H, $C_1$-$C_4$ alkyl, or either of $R^1$ or $R^2$ taken together with $R^3$ represent a 4- to 6-membered saturated ring, or $R^1$ taken together with $R^2$ represent a 3- to 6-membered saturated ring optionally substituted with an O or a N atom;

$R^3$ represents $C_1$-$C_4$ alkyl or $R^3$ taken together with either of $R^1$ or $R^2$ represent a 4- to 6-membered saturated ring; and $R^4$ represents $C_1$-$C_4$ alkyl or $C_1$-$C_4$ haloalkyl;

which comprises:

a) condensing a substituted enone (II),

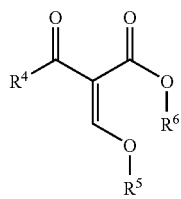

II wherein $R^4$ is as previously defined; and $R^5$ and $R^6$ independently represent $C_1$-$C_4$ alkyl;

with an enamine (III),

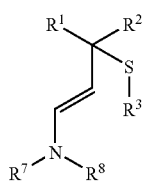

III wherein $R^1$, $R^2$ and $R^3$ are as previously defined; and $R^7$ and $R^8$ independently represent $C_1$-$C_4$ alkyl or $R^7$ and $R^8$ taken together with N represent a 5-membered saturated or unsaturated ring;

b) cyclizing the reaction mixture from step a) in the presence of ammonia or a reagent capable of generating ammonia to produce a 2,3,5-substituted pyridine (IV),

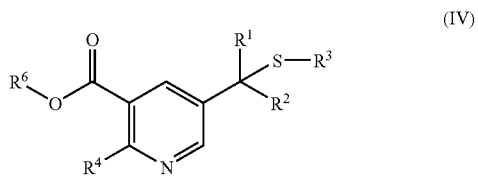

(IV)

wherein $R^1$, $R^2$, $R^3$, $R^4$ and $R^6$ are as previously defined; and c) saponifying and decarboxylating the 2,3,5-substituted pyridine (IV) to give 2-substituted-5-(1-alkylthio)alkylpyridine (I).

The substituted enone (II) starting materials are commercially available or can be prepared from the corresponding keto ester substrates and alkylorthoformates. Typically, acetoacetates are condensed with trialkylorthoformates to yield compounds of type (II). Enamines (III) starting materials can be conveniently prepared from the addition of a suitably substituted amine to an appropriately substituted aldehyde in the presence of a water adsorbing material, with or without a suitable solvent. Typically, the appropriate substituted propionaldehyde is reacted with an anhydrous disubstituted amine at about −20° C. to about 20° C. in the presence of a desiccant such as anhydrous potassium carbonate, and the product is isolated by distillation.

In steps a) and b), approximately equimolar quantities of the substituted enone (II) and the enamine (III) and ammonia are required in the process, although 2-4 fold excesses of the ammonia or the ammonia precursor are often preferred.

Typical reagents capable of generating ammonia include, for example, 1) an ammonium salt of an acid, preferably an organic acid, 2) formamide, or 3) formamide with an acid or acid salt. The ammonium salt of any aliphatic or aromatic organic acid can be used, but for convenience of processing, the ammonium salts of $C_1$-$C_4$ alkanoic acids are preferred. Ammonium formate and ammonium acetate are preferred.

Step a) is illustratively conducted in a polar high-boiling solvent that is miscible with water. Preferred solvents include: amides such as formamide, dimethyl formamide, dimethyl acetamide; alcohols such as methanol, ethanol, isopropanol, (2-methoxy)ethanol; and alkylnitriles including acetonitrile.

The reaction is conducted at a temperature from about −20° C. to about 150° C. Temperatures from about 0° C. to about 80° C. are preferred.

The product is isolated by conventional techniques such as silica gel chromatography or fractional distillation.

In a typical reaction, the substituted enone (II) and enamine (III) are dissolved in the polar solvent at about −5° C. to about 20° C. and agitated until the substituted enone (II) and enamine (III) are consumed. In step b), the ammonium salt of the organic acid is then added, and the mixture is heated at about 50° C. to about 150° C. until the reaction is complete. After dissolving in a non-water miscible solvent and washing with water and, optionally, brine, the 2,3,5-substituted pyridine (IV) is isolated by silica gel column chromatography or by vacuum distillation.

In step c), 2,3,5-substituted pyridine (IV) is saponified by well-known procedures with base, preferably an alkali metal hydroxide such as lithium hydroxide, at about 0° C. to about 50° C. in a polar solvent that is miscible with water, such as tetrahydrofuran. The resulting pyridine carboxylate salt is neutralized and is then decarboxylated by well-known procedures such as, for example, by heating in a high boiling solvent such as DowTherm A (available by The Dow Chemical Company), optionally with copper powder, at temperatures between about 150° C. and about 250° C. to obtain 2-substituted-5-(1-alkylthio)alkylpyridine (I), which can be isolated by conventional methods such as silica gel chromatography or vacuum distillation.

The following examples are presented to illustrate the invention.

EXAMPLES

Example 1

Preparation of 5-(1-Methylthioethyl)-2-trifluoromethylpyridine

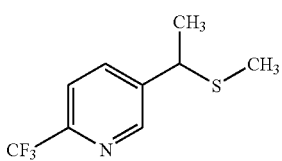

Step 1. Preparation of 1-(3-Methylthiobut-1-enyl)pyrrolidine

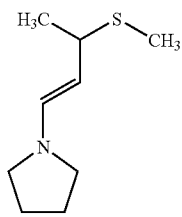

To a dry 5000 milliliter (mL) round bottom flask equipped with mechanical stirrer, nitrogen inlet, addition funnel, and thermometer, was charged 591 g (4.27 moles) of dry granular potassium carbonate and 1428 ml (17.1 moles) of anhydrous pyrrolidine. The mixture was stirred under a atmosphere of nitrogen, and cooled to 4° C. with an ice bath, after which 1050 ml (8.9 moles) of 3-methyl-thiobutyraldehyde was added at a rate that maintains the temperature below 10° C. Upon the completion of the addition, the cooling bath was removed and the reaction was allowed to reach room temperature. The reaction contents were then filtered through a sintered glass filter funnel to remove the solids and the solids were washed with 200 ml of anhydrous ethyl ether. The filtrate was concentrated under vacuum on a rotary evaporator until all of the pyrrolidine was removed to afford 1,519 g of 1-(3-methylthiobut-1-enyl)pyrrolidine as a red liquid. $^1$H NMR CDCl$_3$ δ 1.36 (d, 3H), 1.85 (m, 4H), 2.02 (s, 3H), 3.02 (m, 4H), 3.26 (q, 1H), 3.98 (dd, 1H), 6.25 (d, 1H).

Step 2. Preparation of 5-(1-Methylthioethyl)-2-trifluoromethyl-nicotinic acid ethyl ester

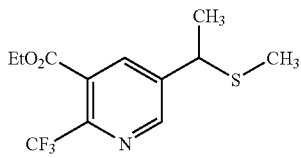

To a dry 50 mL round bottom flask equipped with magnetic stirrer, nitrogen inlet, addition funnel, and thermometer, was charged the 1-(3-methylthiobut-1-enyl)pyrrolidine (5.0 g, 0.0291 mol) and 100 mL of dry acetonitrile. The 2-[1-ethoxymethylidene]-4,4,4-trifluoro-3-oxo-butyric acid ethyl ester (7.0 g, 0.0291 mol) was added dropwise, and the reaction was stirred at room temperature for 1 hour. An aliquot was analyzed by gas chromatography (GC) which indicated that no starting material remained Ammonium acetate (5.0 g, 0.058 mol) was added to the dark red solution and the reaction was heated at reflux for 30 minutes. Cooled and concentrated under vacuum on a rotary evaporator, the crude product was purified by silica gel column chromatography with a gradient of 5% ethyl acetate, 95% hexane to 50% ethyl acetate 50% hexane over 20 minutes to afford 2.5 g of the title compound as a pale yellow oil. $^1$H NMR (CDCl$_3$): δ 1.42 (t, 3H), 1.62 (d, 3H), 1.96 (s, 3H), 3.94 (q, 1H), 4.43 (q, 2H), 8.08 (s, 1H), and 8.71 (s, 1H).

Step 3. Preparation of 5-(1-Methylthioethyl)-2-trifluoromethyl-nicotinic acid

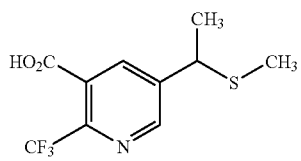

To a dry 50 mL glass vial equipped with magnetic stirrer, and nitrogen inlet, was charged 0.5 g (0.00170 moles) of 5-(1-methylthioethyl)-2-trifluoromethylnicotinic acid ethyl ester, and 10 mL of tetrahydrofuran (THF). The solution was cooled to about 0° C. and 5.1 mL of 1N aqueous lithium hydroxide solution (0.00511 moles) was added slowly via syringe. The reaction was stirred at 0° C. for 1 hour, then overnight at ambient temperature. An aliquot was analyzed by thin layer chromatography (TLC) and high performance liquid chromatography (HPLC), which indicated that the reaction was essentially complete. The mixture was acidified to pH=2 with 1 M aqueous hydrochloric acid, and extracted with 3 aliquots of 50 mL of ethyl acetate. The extract was dried over anhydrous magnesium sulfate (MgSO$_4$), filtered, and concentrated under vacuum on a rotary evaporator to afford 0.410 g of the title compound as a tan solid. $^1$H NMR (CDCl₃): δ 1.66 (d, 3H), 1.96 (s, 3H), 3.98 (q, 1H), 8.01 (bs, 1H), 8.30 (s, 1H), and 8.80 (s, 1H).

Step 4. Preparation of
5-(1-Methylthioethyl)-2-trifluoromethyl-pyridine

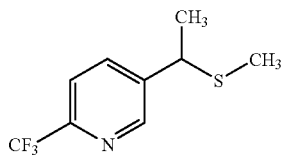

To a dry 50 mL round bottom flask equipped with magnetic stirrer, nitrogen inlet, thermometer, and reflux condenser was charged 0.35 g (0.00132 moles) of 5-(1-methylthioethyl)-2-trifluoromethylnicotinic acid, 0.17 g (0.00264 moles) of copper powder and 10 mL of DowTherm A. The reaction was heated at 240° C. for 1 hour, then cooled to room temperature. The reaction mixture was extracted with 3 aliquots of 50 mL of ethyl acetate, and washed with 50 mL of water and 50 mL of saturated aqueous sodium chloride solution. The organic extract was dried over anhydrous magnesium sulfate, filtered, and concentrated under vacuum on a rotary evaporator. The crude product thus obtained was chromatographed on silica gel with a gradient of 100% hexane to 50% ethyl acetate, 50% hexane. The pure fractions were combined, and concentrated under vacuum on a rotary evaporator to afford 0.13 g of the title compound as a pale yellow oil. ¹H NMR (CDCl₃): δ 1.62 (d, 3H), 1.94 (s, 3H), 3.93 (q, 1H), 7.68 (d, 1H), 7.90 (d, 1H), and 8.66 (s, 1H).

What is claimed is:
1. A compound of the Formula (IV)

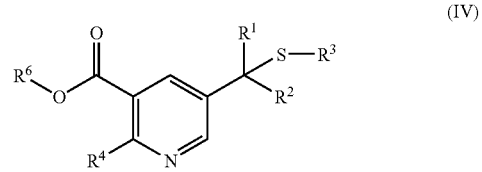

wherein
$R^1$ and $R^2$ independently represent H, or $C_1$-$C_4$ alkyl;
$R^3$ represents $C_1$-$C_4$ alkyl;
$R^4$ represents $C_1$-$C_4$ haloalkyl; and
$R^6$ represents H or $C_1$-$C_4$ alkyl.
2. A compound of claim 1 in which $R^4$ represents $CF_3$.

* * * * *